United States Patent [19]

Rovnyak

[11] 4,341,797
[45] Jul. 27, 1982

[54] BIS-(AMIDINE PHENYL)CYCLOHEXANECARBOXYLIC ACID KETONES, COMPOSITIONS CONTAINING SAME AND METHOD OF USE

[75] Inventor: George C. Rovnyak, Hopewell, N.J.

[73] Assignee: E. R. Squibb & Sons, Inc., Princeton, N.J.

[21] Appl. No.: 270,720

[22] Filed: Jun. 5, 1981

[51] Int. Cl.³ .................. C07C 123/00; A61K 31/195
[52] U.S. Cl. ..................................... 424/319; 562/440
[58] Field of Search ......................... 562/440; 560/35; 424/309, 319

[56] References Cited

PUBLICATIONS

"Synthese von α,α'-Bis-[amidinobenzyliden]-und α,α'-Bis-[amidinobenzyl]-cycloalkanonen," Wagner et al, Pharmazie 32, pp. 141-145, (1977).

*Primary Examiner*—Natalie Trousof
*Assistant Examiner*—James H. Reamer
*Attorney, Agent, or Firm*—Lawrence S. Levinson; Burton Rodney

[57] ABSTRACT

Bis-(amidine phenyl)cyclohexanecarboxylic acid ketones are provided having the structure

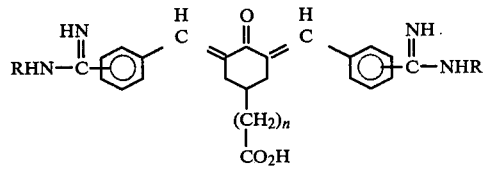

wherein R is hydrogen, lower alkyl or aryl and n is 0, 1 or 2, and acid-addition salts thereof. In addition, pharmaceutical compositions containing the above compounds and a method of using same to treat inflammatory conditions in mammalian species are also provided.

8 Claims, No Drawings

BIS-(AMIDINE PHENYL)CYCLOHEXANECARBOXYLIC ACID KETONES, COMPOSITIONS CONTAINING SAME AND METHOD OF USE

FIELD OF THE INVENTION

The present invention relates to bis-(amidine phenyl)-cyclohexanecarboxylic acid ketones, anti-inflammatory compositions containing same, and to a method for treatment of inflammatory conditions employing the above compounds.

DESCRIPTION OF THE INVENTION

The bis-(amidine phenyl)cyclohexanecarboxylic acid ketones of the invention have the following formula

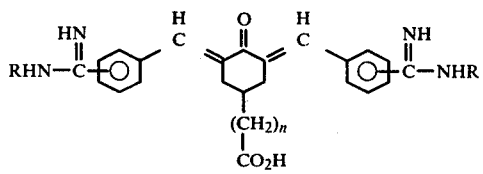

wherein R is H, lower alkyl or aryl and n is 0, 1 or 2.

The compounds of Formula I will preferably be in the form of their acid-addition salts with inorganic and organic acids. Illustrative of such acid salts are the hydrohalides, especially the hydrochloride and hydrobromide which are preferred, sulfate, nitrate, phosphate, borate, acetate, tartrate, maleate, citrate, succinate, oxalate, benzoate, ascorbate, salicylate, methanesulfonate, benzenesulfonate, toluenesulfonate and the like.

Preferred are those compounds of Formula I wherein R is H or lower alkyl, n is 0 or 1 and the

 group is in the meta- or para-position of each of the phenyl groups, in the form of the hydrohalide salt, especially the HCl salt.

The terms "lower alkyl" and "lower alkoxy" as used throughout the specification (by themselves or as part of a larger group) refer to groups having 1 to 8 carbon atoms. Alkyl and alkoxy groups having 1 to 3 carbon atoms are preferred.

The term "aryl" as used throughout the specification (by itself or as part of a larger group) refers to phenyl or phenyl substituted with a lower alkyl, lower alkoxy, halogen or trifluoromethyl group. Phenyl is the preferred aryl group.

The term "halogen" as used throughout the specification refers to fluorine, chlorine, bromine, and iodine; fluorine and chlorine are preferred.

The Formula I compounds of the invention are prepared by condensing an amidino benzaldehyde II with a ketone III employing a molar ratio of II:III of from about 2:1 to about 4:1, preferably from 2.0:1 to about 2.5:1, and optimally about 2:1, using acid catalysis. Although the condensation proceeds in hot (about 100° C.) 85% H₃PO₄ and the product can, after isolation, be converted to the hydrohalide salt, the preferred conditions for preparing the compounds of Formula I involve heating the reactants II and III in 5–10% aqueous mineral or other acid, preferably hydrochloric acid, at reflux temperature for one to eight hours, preferably one to two hours. The product I in the form of the amidine acid-addition salt is collected from the cooled solution and can be recrystallized, if necessary, for example, from 0 to 5% aqueous hydrochloric acid

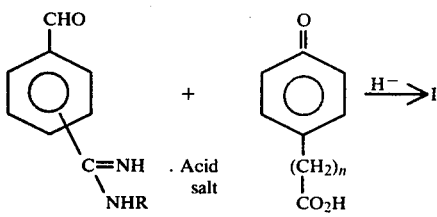

wherein R is as defined above with respect to the Formula I compounds.

The amidine acid-addition salt I may be converted to the free base I of the invention as follows.

The amidine acid-addition salt I, dissolved or suspended in water, is neutralized with exactly two equivalents of aqueous sodium hydroxide and extracted several times with chloroform. The organic extracts are washed with saturated brine, dried over anhydrous magnesium sulfate and concentrated in vacuo to give the free base I. If necessary, the free amidine base I can be recrystallized from a suitable solvent (e.g., ethanol, dioxane, benzene, carbon tetrachloride and combinations thereof).

The amidino benzaldehyde II may be prepared by methods reported in East German Pat. No. 109,864 and Pharmazie, 32, 39 (1977). These methods proceed through the intermediate iminoether acid salt (such as the hydrochloride) IV. In Method A, the iminoether acid salt (hydrochloride) IV is converted to the amidino benzaldehyde II (where R is H) with aqueous methanolic ammonium chloride. In Method B, the iminoether acid salt (such as the hydrochloride) IV is initially converted to ketal V with triethylorthoformate in methanol. The ketal V is converted to amidine VI with the appropriate amine NH₂R in methanol and the amidine VI is transformed to the amidino benzaldehyde II with aqueous methanolic hydrochloric acid or other acid. Method B is preferred because it allows for the introduction of different R groups

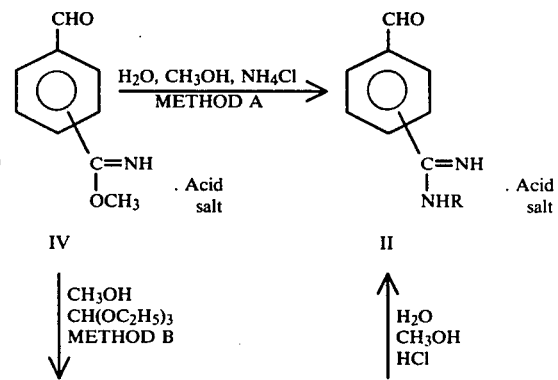

-continued

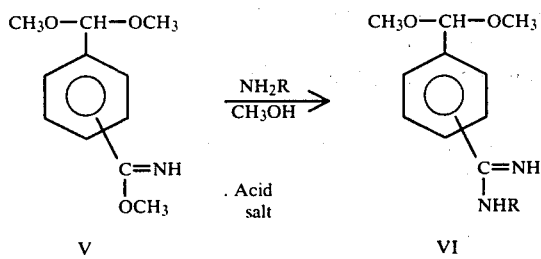

The ketones of Formula III are prepared by known literature methods as described in Ann. Chem., 53, 1811 (1963), CA 60:11910h, and J. Org. Chem., 30, 4145 (1965), CA 64:9607c.

Amidines are strongly basic compounds and react with acids to form salts, such as hydrochlorides, sulfates, sulfonates, acetates, nitrates, carbonates, etc. [S. R. Sandler and W. Karo, "Organic Functional Group Preparations," Vol. III, Chap. 6, Academic Press, New York (1972)].

The free base can be combined with an excess, preferably with 2.2 to 3.0 equivalents, of the desired acid in an appropriate solvent, such as aqueous ethanol (or acetone dioxane, etc.) to give the amidine acid-addition salt.

Alternatively, one amidine acid-addition salt may be converted to another acid-addition salt by mixing with an excess (at least 10-100 fold) of the second acid (or its sodium, potassium or ammonium salt) in an appropriate solvent. For example, the amidine hydrochloride can be mixed with an excess of sodium acetate in warm water (or appropriate solvent mixture) to give the amidine acetate upon cooling [J. Chem. Soc., 1996 (1949)].

The compounds of the invention have anti-inflammatory activity as measured by the mouse active arthus (MAA) test (Goldlust, M. B., Harrity, T. W. and Palmer, D. M., "Evaluation of Anti-Rheumatic Drugs Using the Cutaneous Arthus Reaction," *Recognition of Anit-Rheumatic Drugs*, D. C. Dumonde and M. K. Jasani, MTP Press, Lancaster (1978), pp. 119-136), a Forssman anaphylaxis assay (a variation of the test described by Otterness, Ivan G., Torchia, Anthony J., and Doshan, Harold D., "Complement Inhibition by Amidines and Guanidines - In Vivo and In Vitro Results, " Bio Chem. Pharm., Vol. 27, pp. 1873-1878 (1978)) and other related tests and are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis. Compounds of formula I may be compounded for such use according to accepted pharmaceutical practice in oral dosage forms, such as tablets, capsules, elixirs or powders or in injectable form for administration of about 100 mg to 2 gm per day, preferably 100 mg to 1 gm per day in two to four divided doses.

The following Examples further illustrate and represent preferred embodiments of the invention. All temperatures are expressed in degrees Centigrade.

EXAMPLE 1

3,5-Bis[[4-(aminoiminocarbonyl)phenyl]methylene]-4-oxocyclohexanecarboxylic acid, hydrochloride (1:2)

A. p-Amidinobenzaldehyde hydrochloride

Ref. E. German Pat. No. 109,864; Farmdoc 11059W.

To a solution of 4-cyanobenzaldehyde (10 g, 0.076 mole) in dioxane (30 ml), Et$_2$O (11 ml) and MeOH (7.2 g) (all solvents dried before use) is added dry HCl gas (21.2 g, passed through two H$_2$SO$_4$ towers) at ice bath temperature. The solution is left at 0°-5° for 92 hours, then poured into 200 ml of Et$_2$O and stirred for 1 hour. The imino ether hydrochloride is collected and washed with ether, then dissolved in 75 ml H$_2$O, made alkaline with 10% NaOH and extracted with ether (2x). The extracts are washed with saturated brine (2x), dried (MgSO$_4$) and concentrated in vacuo to give 9.2 g of semi-solid iminoether free base.

The iminoether is dissolved in 100 ml MeOH and treated with 34 mol of 10% aqueous NH$_4$Cl and heated at 90° (oil bath) for 2 hours. The cooled mixture is poured into 400 ml Et$_2$O; the oil that separates is diluted with 40 ml MeOH and poured into 400 ml acetone. The precipitate that forms (1.73 g, NH$_4$Cl) is removed by filtration and the filtrate is diluted with another 200 ml acetone, whereupon product precipitates to give 2.9 g, m.p. 195°-220°. The filtrate, after concentration in vacuo to remove MeOH and H$_2$O, is treated again with acetone, giving an additional 3.81 g, m.p. 210°-220°. The combined product is stirred with ethereal HCl for 1 hour, filtered and washed with fresh ether to give 6.7 g, m.p. 211°-212°.

B.

3,5-Bis[[4-(aminoiminocarbonyl)phenyl]methylene]-4-oxocyclohexanecarboxylic acid, hydrochloride (1:2)

A mixture of 2.6 g (0.014 mole) of 4-amidinobenzaldehyde hydrochloride and 1.0 g (0.007 mole) of 4-carboxy cyclohexanone (preparation as described in CA 59: 12756a) in 50 ml of 10% HCl is stirred and heated at 95°-100° for one hour. Upon cooling, the product is filtered to give 1.9 l g, m.p. 300°-305° dec. Recrystallization from 20 ml of 5% HCl gives 1.6 g (46%) m.p. 313°-315° dec.

EXAMPLE 2

3,5-Bis[[3-(aminoiminocarbonyl)phenyl]methylene]-4-oxocyclohexanecarboxylic acid, hydrochloride (1:2)

A. 3-Amidinobenzaldehyde hydrochloride

A solution of 3-cyanobenzaldehyde (30 g, 0.23 mole) in dioxane (90 ml), ether (33 ml) and methanol (22.2 g) is treated at 0° (ice bath) with 62 g of HCl gas under anhydrous conditions. Solvents are dried and the HCl gas is passed through two concentrated H$_2$SO$_4$ drying towers. After 24 hours at 0°-5° the reaction is filtered into 1400 ml of Et$_2$O. The solid that eventually forms is collected washed with Et$_2$O and dried in vacuo at 60° over KOH to give 40 g of the iminoether hydrochloride, m.p. 108°-110° (lit, m.p. 123°-5°).

The iminoether hydrochloride obtained above (6 g, 0.03 mole) is dissolved in ice water, made basic with 10% NaOH and rapidly extracted with Et$_2$O (2x). The extracts are washed with saturated brine (2x), dried (MgSO$_4$) and concentrated in vacuo to give the free base (4.9 g). This is dissolved in MeOH (25 ml) and 10% aqueous NH$_4$Cl (18 ml) and heated (100° oil bath) for 3 hours. Upon cooling, the mixture is poured onto Et₂O (300 ml) and the oil that separates is collected and treated with acetone (300 ml). The supernatant is decanted from a tacky solid and concentrated in vacuo to remove all solvent, including residual water. The residue, upon trituration with fresh acetone, affords 3.2 g (57%) of product, m.p. 153°–7° (lit m.p. 152°–4°).

EXAMPLES 3 to 7

Using the procedure described in Example 2 and employing the benzaldehyde derivative in Column I and the cyclic ketone derivative in Column II, there is obtained the product in Column III (Table I).

fluoromethyl group, and n is 0, 1 or 2, or pharmaceutically acceptable acid-addition salts thereof.

2. The compound as defined in claim 1 wherein the

is in the metal or para-position.

3. The compound as defined in claim 1 wherein R is H or lower alkyl.

4. The compound as defined in claim 1 wherein n is 0 or 1.

TABLE I (Table I contents: structures for Examples 3–7 in Columns I, II, III)

What is claimed is:

1. A compound of the structure

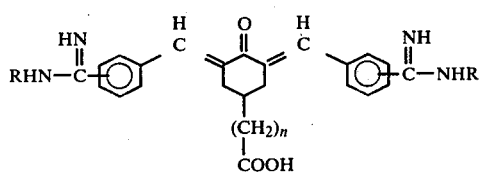

wherein R is H, lower alkyl, phenyl or phenyl substituted with a lower alkyl, lower alkoxy, halogen or tri- 5. The compound as defined in claim 1 having the name 3,5-bis[[4-(aminoiminocarbonyl)phenyl]methylene]-4-oxocyclohexanecarboxylic acid, or its hydrochloride salt.

6. The compound as defined in claim 1 having the name 3,5-bis[[3-(aminoiminocarbonyl)phenyl]methylene]-4-oxocyclohexanecarboxylic acid or its hydrochloride salt.

7. An anti-inflammatory composition comprising a therapeutically effective amount of a compound as defined in claim 1 in a physiologically aceptable carrier therefor.

8. A method for treating an inflammatory condition in a mammalian host, which comprises administering an effective amount of the composition as defined in claim 7.

* * * * *

UNITED STATES PATENT AND TRADEMARK OFFICE
CERTIFICATE OF CORRECTION

PATENT NO. : 4,341,797
DATED : July 27, 1982
INVENTOR(S) : George C. Rovnyak

It is certified that error appears in the above—identified patent and that said Letters Patent is hereby corrected as shown below:

Column 1, next to the first structure, insert --I--.
Column 2, line 10, " $\xrightarrow{H^-}$ " should read -- $\xrightarrow{H^+}$ --.
Column 5 and 6, Table I, Ex. 5, Column III, next to the structure insert -- .2HCl --.
Column 6, line 9, "metal" should read -- meta- --.

Signed and Sealed this

Twenty-first Day of September 1982

[SEAL]

Attest:

GERALD J. MOSSINGHOFF

Attesting Officer  Commissioner of Patents and Trademarks